United States Patent
Gerlach et al.

(10) Patent No.: US 6,184,221 B1
(45) Date of Patent: Feb. 6, 2001

(54) SULFONAMIDE-SUBSTITUTED COMPOUNDS, PROCESSES FOR THEIR PREPARATION, THEIR USE AS A MEDICAMENT OR DIAGNOSTIC, AND MEDICAMENT COMPRISING THEM

(75) Inventors: Uwe Gerlach, Hattersheim; Hans Jochen Lang, Hofheim; Klaus Weidmann, Kronberg; Joachim Brendel, Bad Vilbel, all of (DE)

(73) Assignee: Hoechst Marion Roussel Deutschland GmbH, Frankfurt am Main (DE)

( * ) Notice: Under 35 U.S.C. 154(b), the term of this patent shall be extended for 0 days.

(21) Appl. No.: 09/128,664

(22) Filed: Aug. 4, 1998

(30) Foreign Application Priority Data

Aug. 5, 1997 (DE) ............................. 197 33 779
Oct. 30, 1997 (DE) ............................. 197 47 889

(51) Int. Cl.$^7$ ............ A61K 31/535; C07D 333/52; C07D 413/00; C07D 215/00; A01N 43/12
(52) U.S. Cl. ................... 514/233.5; 514/234.2; 514/234.5; 514/249; 514/253; 514/257; 514/302; 514/318; 514/321; 514/326; 514/443; 514/444; 514/445; 544/116; 544/122; 544/127; 544/129; 544/139; 544/146; 544/230; 544/235; 544/278; 544/350; 544/364; 546/18; 546/113; 546/198; 546/202; 546/207; 546/282.1; 549/50; 549/51; 549/52; 549/58
(58) Field of Search ..................... 544/122, 116, 544/127, 129, 139, 146, 230, 235, 278, 350, 364; 546/18, 113, 198, 202, 207, 282.1; 549/50, 51, 52, 55; 514/233.5, 234.2, 234.5, 249, 253, 257, 302, 318, 321, 326, 443, 444, 445

(56) References Cited

FOREIGN PATENT DOCUMENTS

| | | |
|---|---|---|
| 5539798A | 9/1998 | (AU) . |
| 2205477 | 11/1997 | (CA) . |
| 0 360 62 A1 | 3/1990 | (EP) . |
| 0 807 629 A1 | 11/1997 | (EP) . |
| 0 860 440 A1 | 8/1998 | (EP) . |
| WO 95/14470 | 6/1995 | (WO) . |

OTHER PUBLICATIONS

Busch, A.E., et al., "Role of the $I_{SK}$ Protein in the $I_{minK}$ Channel Complex," TiPS, vol. 18 (Jan. 1997), pp. 26–29.

Soll, R.M., et al., "N–Sulfonamides of Benzopyran–Related Potassium Channel Openers: Conversion of Glyburide Insensitive Smooth Muscle Relaxants to Potent Smooth Muscle Contractors," Bioorganic & Medicinal Chemistry Letters, vol. 4, No. 5 (1994) pp. 769–773.

Colatsky, T.J., et al., "Potassium Channel Blockers as Antiarrhythmic Drugs," Drug Development Research, vol. 33 (1994), pp. 235–249.

Buckle, D.R., et al., "Structural Modifications of the Potassium Channel Activator Cromakalim: The C–3 Position," J. Chem. Soc. Perkin Trans., vol. 1 (1991), pp. 63–70.

Busch, A.E., et al., "The Novel Class III Antiarrhythmics NE–10064 and NE–10133 Inhibit $I_{SK}$ Channels Expressed in Xenopus Oocytes and $I_{KS}$ in Guinea Pig Cardiac Myocytes," Biochem. Biophys. Res. Commun., vol. 202 (1994), pp. 265–270.

Colatsky, T.J., et al., "Channel Specificity in Antiarrhythmic Drug Action," Circulation, vol. 82 (1990), pp. 2235–2242.

Roden, D.M., "Current Status of Class III Antiarrhythmic Drug Therapy," Am. J. Cardiol., vol. 72 (1993), pp. 44B–49B.

H. Suessbrich et al., "Specific Blockade of Slowly Activating $I_{sK}$ Channels by Chromanols—Impact on the Role of $I_{sK}$ Channels in Epithelia," FEBS Letters 396, (1996), pp. 271–275.

E. Lohrmann et al., "A New Class of Inhibitors of cAMP–Mediated Cl⁻Secretion in Rabbit Colon, Acting by the Reduction of cAMP–Activated K⁺Conductance," Pflügers Arch—Eur. J. Physiol, (1995), vol. 429, pp. 517–530.

Primary Examiner—John Kight
Assistant Examiner—Raymond Covington
(74) Attorney, Agent, or Firm—Finnegan, Henderson, Farabow, Garrett & Dunner, L.L.P.

(57) ABSTRACT

Compounds of the formula I

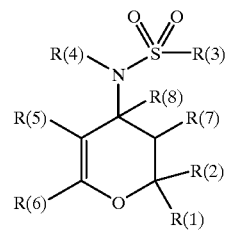

having the meanings of the substituents indicated in the claims are outstandingly active substances for the production of medicaments for the prophylaxis and for the therapy of cardiovascular disorders, in particular arrhythmias, for the treatment of ulcers of the gastrointestinal region or for the treatment of diarrheal illnesses.

28 Claims, No Drawings

SULFONAMIDE-SUBSTITUTED COMPOUNDS, PROCESSES FOR THEIR PREPARATION, THEIR USE AS A MEDICAMENT OR DIAGNOSTIC, AND MEDICAMENT COMPRISING THEM

The present case claims priority of German Patent Application 19733779.1, filed Aug. 5, 1997, and German Patent Application 19747889.1, filed Oct. 30, 1997, both of which are incorporated by reference.

DESCRIPTION

The invention relates to compounds of the formula I

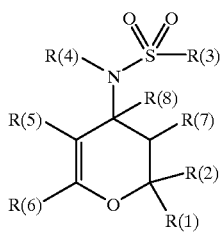

I in which R(1), R(2), R(3), R(4), R(5), R(6), R(7) and R(8) have the meanings indicated in the following, their preparation and their use, in particular in pharmaceuticals.

The compounds affect the potassium channel opened by cyclic adenosine monophosphate (cAMP) or the $I_{K_s}$ channel and are outstandingly suitable as pharmaceutical active compounds, for example for the prophylaxis and therapy of cardiovascular disorders, in particular arrhythmias, for the treatment of ulcers of the gastrointestinal region or for the treatment of diarrheal illnesses.

In pharmaceutical chemistry, the 4-acylaminochroman derivatives class has been worked on intensively in recent years. The most prominent representative of this class is cromakalim of the formula A (J. Chem. Soc. Perkin Trans. 1, 1991, 63–70).

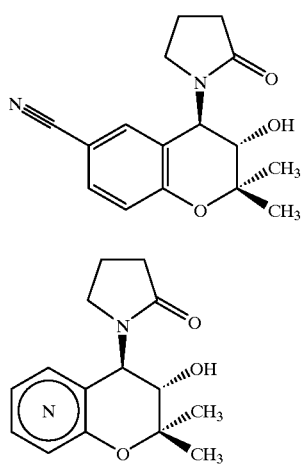

A

B

Cromakalim and other related 4-acylaminochroman derivatives are compounds having a relaxant action on smooth muscular organs, so that they are used for lowering raised blood pressure as a result of vascular muscle relaxation and in the treatment of asthma as a result of the relaxation of the smooth musculature of the airways. It is common to all these preparations that they act at the cellular level, for example, of smooth muscle cells and lead there to an opening of specific ATP-sensitive K⁺ channels. The increase in negative charge in the cell (hyperpolarization) induced by the efflux of $K^+$ ions counteracts via secondary mechanisms the increase in the intracellular $Ca^{2+}$ concentration and thus cell activation which leads, for example, to muscle contraction.

Similar structures to those of the formula I, the so-called pyranopyridines (formula B), are described in the literature. However, we are also dealing here exclusively with 4-acylamino derivatives, which likewise have K-ATP channel-blocking properties.

The compounds of the formula I according to the invention differ structurally from these acylamino derivatives, inter alia by the replacement of the acylamino group by a sulfonylamino function. While cromakalim (formula A) and analogous acylamino compounds act as openers of ATP-sensitive $K^+$ channels, the compounds of the formula I according to the invention having the sulfonylamino structure, however, do not show any opening action on this $K^+$ (ATP) channel, but surprisingly show a strong and specific blocking (closing) action on a $K^+$ channel which is opened by cyclic adenosine monophosphate (CAMP) and differs fundamentally from the $K^+$ (ATP) channel mentioned. More recent investigations show that this $K^+$ (cAMP) channel identified in colonic tissue is very similar, perhaps even identical, to the $I_{K_s}$ channel identified in the cardiac muscle. In fact, it was possible, for the compounds of the formula I according to the invention, to show a strong blocking action on the $I_{K_s}$ channel in guinea-pig cardiomyocytes and on the $I_{sK}$ channel expressed in Xenopus oocytes. As a result of this blocking of the $K^+$ (cAMP) channel or of the $I_{K_s}$ channel, the compounds according to the invention display pharmacological actions of high therapeutic utility in the living body.

The present invention relates to compounds of the formula I

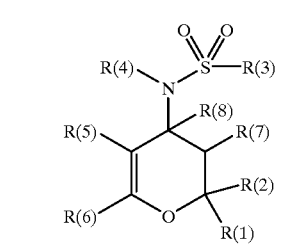

I in which:
R(1) and R(2) independently of one another are hydrogen, $CF_3$, $C_2F_5$, $C_3F_7$, alkyl having 1, 2, 3, 4, 5, or 6 carbon atoms, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
or
R(1) and R(2) together are an alkylene chain having 2, 3, 4, 5, 6, 7, 8, 9, or 10 carbon atoms;
  where one $CH_2$ group of the alkylene chain can be replaced by —O—, —CO—, —S—, —SO—, —$SO_2$—, or —NR(10)—;
  R(10) is hydrogen or alkyl having 1, 2, or 3 carbon atoms;
R(3) is R(12)—$C_aH_{2a}$[NR(13)]$_m$—;
R(12) is hydrogen or cycloalkyl having 3, 4, 5, 6, 7, or 8 carbon atoms, $CF_3$, $C_2F_5$, or $C_3F_7$;

a is zero, 1, 2, 3, 4, 5, 6, 7, 8, 9, or 10;

m is zero or 1;

R(13) is hydrogen or alkyl having 1, 2, 3, 4, 5, or 6 carbon atoms;

or

R(12) and R(13) together are an alkylene chain having 4, 5, 6, 7, or 8 carbon atoms, where one $CH_2$ group of the alkylene chain can be replaced by —O—, —[$SO_{zero,\ 1,\ or\ 2}$]—, —CO—, or —NR(10)—;

R(10) is hydrogen or alkyl having 1, 2, or 3 carbon atoms;

R(4) is R(14)—$C_rH_{2r}$;

r is zero, 1, 2, 3, 4, 5, 6, 7, 8, 9, 10, 11, 12, 13, 14, 15, 16, 17, 18, 19, or 20;

R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl, wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;

where one $CH_2$ group of the group $C_rH_{2r}$ can be replaced by —O—, —CH=CH—, —C≡C—, —CO—, —CO—O—, —CO—NR(11)—, —[$SO_{zero,\ 1,\ or\ 2}$]—, or —NR(11)—;

R(11) is hydrogen or —($C_aH_{2a}$)—R(10);

where one $CH_2$ group of the group $C_aH_{2a}$ can be replaced by —O—, —CH=CH—, —C≡C—, —CO—, —CO—O—, —O—CO—, —S—, —SO—, —$SO_2$—, —NR(10)—, or —CONR(10)—;

R(10) is hydrogen or alkyl having 1, 2, or 3 carbon atoms;

a is zero, 1, 2, 3, 4, 5, 6, 7, 8, 9, or 10;

or

R(3) and R(4) together are an alkylene chain having 3, 4, 5, 6, 7, or 8 carbon atoms, where one $CH_2$ group of the alkylene chain can be replaced by —O—, —[$SO_{zero,\ 1,\ or\ 2}$]—, —CO—, or —NR(11)—;

R(11) is hydrogen or —($C_aH_{2a}$)—R(10), where one $CH_2$ group of the group $C_aH_{2a}$ can be replaced by —O—, —CH=CH—, —C≡C—, —CO—, —CO—O—, —O—CO—, —S—, —SO—, —$SO_2$—, NR(10)—, or —CONR(10)—;

R(10) is hydrogen or alkyl having 1, 2, or 3 carbon atoms;

a is zero, 1, 2, 3, 4, 5, 6, 7, 8, 9, or 10;

R(5) and R(6) are

—CR(15)=CR(16)—CR(17)=N—,

—CR(15)=CR(16)—N=CR(17)—,

—CR(15)=N—CR(17)=N—,

—CR(15)=N—N=CR(17)—,

—N=CR(16)—CR(17)=N—, or

—S—CR(15)=CR(16)—;

R(15), R(16) and R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl, wherein said phenyl is unsubstituted or substituted by 1 or 2 identical or different substituents that are F, Cl, Br, I, $CF_3$, methyl, methoxy, sulfamoyl, or methylsulfonyl;

R(19) is hydrogen or alkyl having 1, 2, or 3 carbon atoms;

R(21) is hydrogen, methyl, ethyl, phenyl, or —$C_uH_{2u}$—NR(19)R(20);

wherein said phenyl is unsubstituted or substituted by 1 or 2 identical or different substituents that are F, Cl, Br, I, $CF_3$, methyl, methoxy, sulfamoyl, or methylsulfonyl;

R(20) is hydrogen or alkyl having 1, 2, or 3 carbon atoms;

u is 2 or 3;

R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl, wherein said phenyl is unsubstituted or substituted by 1 or 2 identical or different substituents that are F, Cl, Br, I, $CF_3$, methyl, methoxy, sulfamoyl, or methylsulfonyl;

s is zero, 1, 2, 3, 4, 5, or 6;

Z is —[$S(O)_{zero,\ 1,\ or\ 2}$]—, —CO—, —$SO_{(zero,\ 1,\ or\ 2)}$—NR(11)—, —$SO_2$—O—, —O—, —NR(11)—, or —[CO—NR(11)]—;

R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms;

R(8) is hydrogen or alkyl having 1, 2, 3, 4, 5, or 6 carbon atoms;

and their physiologically tolerable salts.

Preferred compounds of the formula I are those in which:

R(1) and R(2) independently of one another are hydrogen, $CF_3$, $C_2F_5$, $C_3F_7$, alkyl having 1, 2, 3, 4, 5, or 6 carbon atoms, or phenyl, wherein said phenyl is unsubstituted or substituted by 1 or 2 identical or different substituents that are F, Cl, Br, I, $CF_3$, methyl, methoxy, sulfamoyl, or methylsulfonyl;

or

R(1) and R(2) together are an alkylene chain having 2, 3, 4, 5, 6, 7, 8, 9, or 10 carbon atoms; where one $CH_2$ group of the alkylene chain can be replaced by —O—, —CO—, —S—, —SO—, —$SO_2$—, or —NR(10)—;

R(10) is hydrogen or alkyl having 1, 2, or 3 carbon atoms;

R(3) is R(12)—$C_aH_{2a}$[NR(13)]$_m$—;

R(12) is hydrogen or cycloalkyl having 3, 4, 5, 6, 7, or 8 carbon atoms, $CF_3$, $C_2F_5$, or $C_3F_7$;

a is zero, 1, 2, 3, 4, 5, 6, 7, 8, 9, or 10;

m is zero or 1;

R(13) is hydrogen or alkyl having 1, 2, 3, 4, 5, or 6 carbon atoms;

R(4) is R(14)—$C_rH_{2r}$;

r is zero, 1, 2, 3, 4, 5, 6, 7, 8, 9, 10, 11, 12, 13, 14, 15, 16, 17, 18, 19, or 20;

R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl, wherein said phenyl is unsubstituted or substituted by 1 or 2 identical or different substituents that are F, Ci, Br, I, $CF_3$, methyl, methoxy, sulfamoyl, methylsulfonyl, or methylsulfonylamino;

where one $CH_2$ group of the group $C_rH_{2r}$ can be replaced by —O—, —CH=CH—, —C≡C—, —CO—, —CO—O—, —CO—NR(11)—, —[$SO_{zero,\ 1,\ or\ 2}$]—, or —NR(11)—;

R(11) is hydrogen or —($C_aH_{2a}$)—R(10) where one $CH_2$ group of the group $C_aH_{2a}$ can be replaced by —O—, —CH=CH—, —C≡C—, —CO—, —CO—O—, —O—CO—, —S—, —SO—, —$SO_2$—, NR(10)—, or —CONR(10)—;

a is zero, 1, 2, 3, 4, 5, 6, 7, 8, 9, or 10;
R(5) and R(6) are
—CR(15)=CR(16)—CR(17)=N—,
—CR(15)=CR(16)—N=CR(17)—, —CR(15)=N—CR(17)=N—,
—CR(15)=N—N=CR(17)—,
—N=CR(16)—CR(17)=N—, or
—S—CR(15)=CR(16)—;

R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;

R(19) is hydrogen or alkyl having 1, 2, or 3 carbon atoms;
R(21) is hydrogen, methyl, ethyl, phenyl, or —$C_uH_{2u}$—NR(19)R(20);
  wherein said phenyl is unsubstituted or substituted by 1 or 2 identical or different substituents that are F, Cl, Br, I, $CF_3$, methyl, methoxy, sulfamoyl, or methylsulfonyl;
u is 2 or 3;
R(20) is hydrogen or alkyl having 1, 2, or 3 carbon atoms;
R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
  wherein said phenyl is unsubstituted or substituted by 1 or 2 , identical or different substituents that are F, Cl, Br, I, $CF_3$, methyl, methoxy, sulfamoyl, or methylsulfonyl;
s is zero, 1, 2, 3, 4, 5, or 6;
Z is —[S(O)$_{zero, 1, or 2}$]—, —CO—, —$SO_2$—NR(11)—, —$SO_2$—O—, —NR(11)—, or —[CO—NR(11)]—;
R(7) is hydrogen, hydroxyl, alkoxy having 1, 2, 3, or 4 carbon atoms, acyloxy having 1, 2, 3 or 4 carbon atoms, Cl, Br, F, or alkyl having 1, 2, 3, or 4 carbon atoms;
R(8) is hydrogen or alkyl having 1, 2, 3, 4, 5, or 6 carbon atoms;
and their physiologically tolerable salts.

Particularly preferred compounds of the formula I are those in which:
R(1) and R(2) independently of one another are hydrogen, $CF_3$, $C_2F_5$, $C_3F_7$, alkyl having 1, 2, 3, 4, 5, or 6 carbon atoms, or phenyl,
  wherein said phenyl is unsubstituted or substituted by 1 or 2 identical or different substituents that are F, Cl, Br, I, $CF_3$, methyl, methoxy, sulfamoyl, or methylsulfonyl; or
R(1) and R(2) together are an alkylene chain having 2, 3, 4, 5, 6, 7, 8, 9, or 10 carbon atoms;
  where one $CH_2$ group of the alkylene chain can be replaced by —O—, —CO—, —S—, —SO—, —$SO_2$—, or —NR(10)—;
R(10) is hydrogen or alkyl having 1, 2, or 3 carbon atoms;
R(3) is R(12)—$C_aH_{2a}$[NR(13)]$_m$—;
R(12) is hydrogen or cycloalkyl having 3, 4, 5, 6, 7, or 8 carbon atoms, $CF_3$, $C_2F_5$, or $C_3F_7$;
a is zero, 1, 2, 3, 4, 5, 6, 7, 8, 9, or 10;
m is zero or 1;

R(13) is hydrogen or alkyl having 1, 2, 3, 4, 5, or 6 carbon atoms;
R(4) is R(14)—$C_rH_{2r}$;
r is 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
  wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;
where one $CH_2$ group of the group $C_rH_{2r}$ can be replaced by —O—, —CH=CH—, —C≡—, —CO—, —CO—O—, —CO—NR(11)—, —[SO$_{zero, 1, or 2}$]—, or —NR(11)—;
R(11) is hydrogen or —($C_aH_{2a}$)—R(10);
  where one $CH_2$ group of the group $C_aH_{2a}$ can be replaced by —O—, —CH=CH—, —C≡C—, —CO—, —CO—O—, —O—CO—, —S—, —SO—, —$SO_2$—, —NR(10)—, or —CONR(10)—;
R(10) is hydrogen or alkyl having 1, 2, or 3 carbon atoms;
a is zero, 1, 2, 3, 4, 5, 6, 7, 8, 9, or 10;
R(5) and R(6) are
—CR(15)=CR(16)—CR(17)=N— or —CR(15)=CR(16)—N=CR(17)—;
R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
R(19) is hydrogen or alkyl having 1, 2, or 3 carbon atoms;
R(21) is hydrogen, methyl, ethyl, phenyl, or —$C_uH_{2u}$—NR(19)R(20);
  wherein said phenyl is unsubstituted or substituted by 1 or 2 identical or different substituents that are F, Cl, Br, I, $CF_3$, methyl, methoxy, sulfamoyl, or methylsulfonyl;
R(20) is hydrogen or alkyl having 1, 2, or 3 carbon atoms;
u is 2 or 3;
R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, or $C_3F_7$, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
s is zero, 1, 2, 3, 4, 5, or 6;
Z is —[S(O)$_{zero, 1, or 2}$]—, —CO—, —$SO_2$—NR(11)—, —$SO_2$—O—, —O—, —NR(11)—, or —[CO—NR(11)]—;
R(7) is hydrogen, hydroxyl, alkoxy having 1, 2, 3, or 4 carbon atoms, alkyl having 1, 2, 3, or 4 carbon atoms;
R(8) is hydrogen or alkyl having 1, 2, 3, 4, 5, or 6 carbon atoms;
and their physiologically tolerable salts.

Very particularly preferred compounds of the formula I are those in which:

R(1) and R(2) independently of one another are hydrogen, $CF_3$, $C_2F_5$, $C_3F_7$, alkyl having 1, 2, 3, 4, 5, or 6 carbon atoms, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
or
R(1) and R(2) together are an alkylene chain having 2, 3, 4, 5, or 6 carbon atoms;
  where one $CH_2$ group of the alkylene chain can be replaced by —O—, —CO—, —S—, —SO—, —$SO_2$—, or —NR(10)—;
R(10) is hydrogen or alkyl having 1, 2, or 3 carbon atoms;
R(3) is R(12)—$C_aH_{2a}$—;
R(12) is hydrogen or cycloalkyl having 3, 4, 5, 6, 7, or 8 carbon atoms, $CF_3$, $C_2F_5$, or $C_3F_7$;
a is zero, 1, 2, 3, 4, 5, 6, 7, 8, 9, or 10;
R(4) is $R(^{14})$—$C_rH_{2r}$—;
r is 1, 2, 3, 4, 5, 6, 7, 8, 9, 10, 11, 12, or 13;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
  wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;
  where one $CH_2$ group of the group $C_rH_{2r}$ can be replaced by —O—, —CH=CH—, —C≡C—, —CO—, —CO—O—, —CO—NR(11)—, —[$SO_{zero, 1, or 2}$]—, or —NR(11)—;
R(11) is hydrogen or —($C_aH_{2a}$)—R(10)
  where one $CH_2$ group of the group $C_aH_{2a}$ can be replaced by —O—, —CH=CH—, —C≡C—, —CO—, —CO—O—, —O—CO—, —S—, —SO—, —$SO_2$—, NR(10)—, or —CONR(10)—;
R(10) is hydrogen or alkyl having 1, 2, or 3 carbon atoms;
R(5) and R(6) are
—CR(15)=CR(16)—CR(17)=N— or
—CR(15)=CR(16)—N=CR(17)—;
R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
R(19) is hydrogen or alkyl having 1, 2, or 3 carbon atoms;
R(21) is hydrogen, methyl, ethyl, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
R(22) is hydrogen;
s is zero, 1, 2, 3, 4, 5, or 6;
Z is —[$S(O)_{zero, 1, or 2}$]—, —CO—, —$SO_2$—NR(11)—, —$SO_2$—O—, —O—, —NR(11)—, or —[CO—NR(11)]—;
R(7) is hydrogen, hydroxyl, alkoxy having 1, 2, 3, or 4 carbon atoms, alkyl having 1, 2, 3, or 4 carbon atoms;
R(8) is hydrogen or alkyl having 1, 2, 3, 4, 5, or 6 carbon atoms;
and their physiologically tolerable salts.

If compounds of formula I contain acidic or basic groups or basic heterocycles, the invention relates also to the corresponding pharmacologically or toxicologically tolerable salts. Thus a compound of formula I that carries one or more COOH groups, can be used, for example, as an alkali metal salt, preferably as the sodium or potassium salt. Compounds of formula I that carry basic, protonatable groups or contain basic heterocyclic radicals, can also be used in the form of their organic or inorganic, pharmacologically and toxicologically tolerable acid addition salts, for example as hydrochlorides, methanesulfonates, acetates, lactates, maleates, fumarates, malates, gluconates etc. If the compounds of formula I contain acidic and basic groups in the same molecule, beside the salt forms described, the invention also includes internal salts, so-called betaines.

When appropriately substituted, the compounds of the formula I can be present in stereoisomeric forms. If the compounds of the formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to enantiomers, for example, in enantiomerically pure form, both as levo- and dextrorotatory antipodes, and also in the form of mixtures of the two enantiomers in different ratios or in the form of racemates. If cis/trans isomerism is present, the invention relates both to the cis form and to the trans form and mixtures of these forms. The preparation of individual stereoisomers can be carried out, if desired, by resolution of a mixture according to customary methods or, for example, by stereoselective synthesis. If mobile hydrogen atoms are present, the present invention also comprises all tautomeric forms of the compounds of the formula I.

Alkyl and alkylene chain radicals can be unbranched or branched.

The compounds of the formula I can be prepared by different chemical processes to which the invention likewise relates.

Thus a compound of the formula I is obtained by a) reacting a compound of the formula II

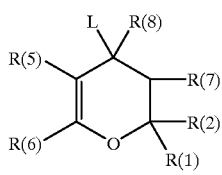

II in which R(1), R(2), R(5), R(6), R(7) and R(8) have the meaning indicated in formula I and L is a customary nucleofugic leaving group, in particular F, Cl, Br, I, $MeSO_2$—O—, a p-toluenesulfonyloxy radical, or R(7) and L together are an epoxide ring, in a manner known per se with a sulfonamide or its salt of the formula III

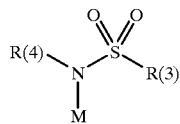

III in which R(3) and R(4) have the meaning indicated in formula I and M is hydrogen or preferably a metal equivalent, particularly preferably lithium, sodium, or potassium;

or by b) reacting a compound of the formula IV

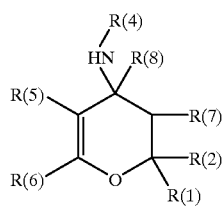

IV in which R(1), R(2), R(4), R(5), R(6), R(7) and R(8) have the meaning indicated in formula I, with a sulfonic acid derivative of the formula V

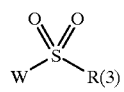

V in which R(3) has the meaning indicated in formula I and W is a nucleofugic leaving group, such as fluorine, bromine, 1-imidazolyl, but in particular chlorine;

or by c) reacting a compound of the formula VI

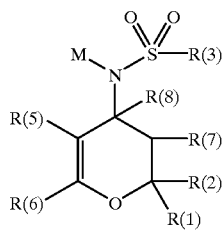

VI in which R(1), R(2), R(3), R(5), R(6), R(7), R(8) and M have the meaning indicated, in a manner known per se in the sense of an alkylation reaction with an alkylating agent of the formula VII

R(4)—L    VII in which R(4), with the exception of hydrogen, and L have the meaning indicated above;

or by d) carrying out, in a compound of the formula I

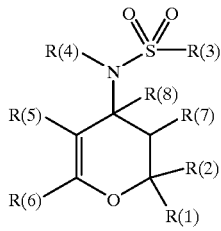

I in which R(1) to R(4), R(7) and R(8) have the meaning indicated, an electrophilic substitution reaction in at least one of the positions R(15), R(16), R(17) of the ring system R(5)-R(6) if this position is hydrogen and the remaining substituents R(1) to R(8) have the meaning indicated in formula I.

Procedure a) describes the reaction of a sulfonamide or of one of its salts of the formula III with a reactive heterocycle of the formula II. As the reaction of a sulfonamide III is carried out from the salt form, when using a free sulfonamide (formula III, M=H) a sulfonamide salt which is distinguished by higher nucleophilicity and thus by higher reactivity must be generated (formula III, M=cation) by the action of a base. If free sulfonamide (M=H) is employed, the deprotonation of the sulfonamide to the salt is carried out in situ, preferably using those bases which are not alkylated or only slightly alkylated themselves, such as sodium carbonate, potassium carbonate, a sterically strongly hindered amine, e.g. dicyclohexylamine, N,N,N-dicyclohexylethylamine or other strong nitrogen bases with low nucleophilicity, for example DBU, N,N',N"'-triisopropylguanidine, etc. However, it is also possible to employ other customarily used bases for the reaction, such as potassium tert-butoxide, sodium methoxide, alkali metal hydrogencarbonates, alkali metal hydroxides, such as, for example, LiOH, NaOH or KOH, or alkaline earth metal hydroxides, for example $Ca(OH)_2$.

The reaction is preferably carried out in polar organic solvents such as dimethylformamide, dimethylacetamide, tetramethylurea, hexamethylphosphoramide, tetrahydrofuran, dimethoxyethane, toluene, a halogenated hydrocarbon such as chloroform or methylene chloride, etc. However, the reaction can also be carried out in polar protic solvents, such as water, methanol, ethanol, isopropanol, ethylene glycol or its oligomers and their corresponding hemiethers and ethers. The reaction is carried out in a preferred temperature range from −10 to 140° C., particularly preferably from 20 to 100° C. Favorably, procedure a) can also be carried out under the conditions of a two-phase catalysis.

The compounds of the formula II are obtained by methods known from the literature, for example from the corresponding unsaturated compound of formula X

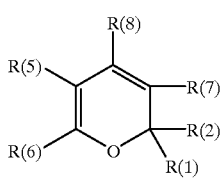

X by the action of an inorganic or organic peroxide, such as, for example, $H_2O_2$, MCPBA, peracetic acid. The addition of halogen/OH is also possible by the reaction of X with NCS, NBS, chlorine or bromine in aqueous solvents. In the case of the epoxide (R(7) and L form an epoxide ring), this can be prepared from the hydrohalide by elimination of H-halogen using various bases. Advantageously, the reaction is carried out in a solvent which is sufficiently inert to these halogenating or oxidizing reagents, such as, for example, in DMSO or halogenated hydrocarbons, such as, for example, chloroform, methylene chloride.

Procedure b) describes the reaction, which is known per se and frequently used, of a reactive sulfonyl compound of the formula V, in particular of a chlorosulfonyl compound (W=Cl), with an amino derivative of the formula IV to give the corresponding sulfonamide derivative of the formula I. In principle, the reaction can be carried out without solvent, but reactions of this type are in most cases carried out using a solvent.

The reaction is preferably carried out using a polar solvent, preferably in the presence of a base which can advantageously be used as a solvent itself, e.g. when using triethylamine, in particular pyridine and its homologs. Solvents likewise used are, for example, water, aliphatic alcohols, e.g. methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPT. The reaction is in this case carried out at a temperature from 0 to 160° C., preferably from 20 to 100° C.

The amino derivatives of the formula IV are obtained in a manner known per se from the literature, preferably by reaction of the reactive compounds of the formula 11 where R(1), R(2), R(5), R(6) and L have the meaning indicated in formula I, either with ammonia or an amine of the formula Xl

  Xl where R(4) has the meaning indicated in formula I.

Procedure c) represents the alkylation reaction known per se of a sulfonamide or of one of its salts VI with an alkylating agent of the formula VII. In accordance with the analogy of the reaction to procedure a), the reaction conditions already described in detail under procedure a) apply to procedure c).

The preparation of the sulfonamide derivatives VI and their precursors has already been described in procedure b). The preparation of the alkylating agents VII is carried out according to analogous procedures in the literature or as described under procedure a), preferably from the corresponding hydroxyl compounds (formula VII where L is —OH).

Procedure d) describes the further chemical conversion of compounds of the formula I according to the invention into other compounds of the formula I by electrophilic substitution reactions in one or more of the positions designated by R(5) to R(8), which in each case are hydrogen.

Preferred substitution reactions are
1. aromatic nitration to introduce one or more nitro groups, and their subsequent reduction to $NH_2^-$,
2. aromatic halogenation, in particular for the introduction of chlorine, bromine or iodine,
3. chlorosulfonation by the action of chlorosulfonic acid, for the introduction of a chlorosulfonyl group,
4. the Friedel-Crafts acylation reaction to introduce an acyl radical according to methods known from the literature.

In all procedures, it may be appropriate to protect functional groups in the molecule temporarily in certain reaction steps. Such protective group techniques are familiar to the person skilled in the art. The choice of a protective group for groups in question and the methods for their introduction and removal are described in the literature and can be adapted to the individual case, where appropriate, without difficulties.

It has already been said that the compounds of the formula I surprisingly have a strong and specific blocking (closing) action on a $K^+$ channel which is opened by cyclic adenosine monophosphate (cAMP) and fundamentally differs from the well-known $K^+$ (ATP) channel, and that this $K^+$ (cAMP) channel identified in colonic tissue is very similar, perhaps even identical, to the $I_{Ks}$ channel identified in the cardiac muscle. For the compounds according to the invention, it was possible to show a strong blocking action on the $I_{Ks}$ channel in guinea-pig cardiomyocytes and on the $I_{sK}$ channel expressed in Xenopus oocytes. As a result of this blocking of the $K^+$ (cAMP) channel or of the $I_{Ks}$ channel, the compounds according to the invention display pharmacological actions of high therapeutic utility in the living body and are outstandingly suitable as pharmaceutical active compounds for the therapy and prophylaxis of various syndromes.

The compounds of the formula I according to the invention are thus distinguished as a novel active compound class of potent inhibitors of stimulated gastric acid secretion.

The compounds of the formula I are thus useful pharmaceutical active compounds for the therapy and prophylaxis of ulcers of the stomach and of the intestinal region, for example of the duodenum. They are likewise suitable, on account of their strong gastric secretion-inhibiting action, as excellent therapeutics for the therapy and prophylaxis of reflux esophagitis.

The compounds of the formula I according to the invention are furthermore distinguished by an antidiarrheal action and are therefore suitable as pharmaceutical active compounds for the therapy and prophylaxis of diarrheal illnesses.

The compounds of the formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially cardiac arrhythmias which can be eliminated by action potential prolongation. They can be specifically used for the therapy and prophylaxis of atrial fibrillation and atrial flutters, and for the therapy and prophylaxis of reentry arrhythmias and for the prevention of sudden heart death as a result of ventricular fibrillation.

Although numerous substances having antiarrhythmic activity are already on the market, there is nevertheless no compound which is really satisfactory with respect to activity, range of application and side-effect profile, so that there is furthermore a need for the development of improved antiarrhythmics.

The action of numerous known antiarrhythmics of the so-called class IIIl is based on an increase in the myocardial refractory time by prolongation of the action potential duration. This is essentially determined by the extent of repolarizing $K^+$ streams which flow out of the cell via various $K^+$ channels. Particularly great importance is ascribed in this context to the so-called "delayed rectifier" $I_K$, of which two subtypes exist, a rapidly activated $I_{Kr}$ and a slowly activated $I_{Ks}$. Most known class III antiarrhythmics block $I_{Kr}$ predominantly or exclusively (e.g. dofetilide, d-sotalol). It has been shown, however, that these compounds have an increased proarrhythmic risk at low or normal heart rates, arrhythmias which are designated as "Torsades de pointes" in particular being observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging action of the $I_{Kr}$ blockers is markedly reduced, which is attributed to the fact that under these conditions the $I_{Ks}$ contributes more strongly to the repolarization. For these reasons, the substances according to the invention, which act as $I_{Ks}$ blockers, have significant advantages compared with the known $I_{Kr}$ blockers. In the meantime, it has also been described that a correlation exists between $I_{Ks}$ channel-inhibitory action and the suppression of life-threatening cardiac arrhythmias, such as are elicited, for example, by β-adrenergic hyperstimulation (e.g. T. J. Colatsky, C. H. Follmer and C. F. Starmer; "Channel Specificity in Antiarrhythmic Drug Action; Mechanism of potassium channel block and its role in suppressing and aggravating cardiac arrhythmias"; Circulation 82 (1990), 2235–2242; A. E. Busch, K. Malloy, W. J. Groh, M. D. Varnum, J. P. Adelman and J. Maylie; "The novel class III antiarrhythmics NE-10064 and NE-10133 inhibit $I_{sK}$ channels in Xenopus oocytes and $I_{Ks}$ in guinea pig cardiac myocytes"; Biochem. Biophys. Res. Commun. 202 (1994), 265–270).

Moreover, the compounds contribute to a marked improvement of cardiac insufficiency, in particular of congestive heart failure, advantageously in combination with contraction-promoting (positively inotropic) active compounds, e.g. phosphodiesterase inhibitors.

In spite of the therapeutically utilizable advantages which can be achieved by a blockade of the $I_{Ks}$, hitherto only very few compounds have been described which inhibit this subtype of the "delayed rectifier". The substance azimilide which is in development admittedly also has a blocking action on the $I_{KS}$, but mainly blocks the $I_{Kr}$ (selectivity 1:10). WO-A-95/14470 claims the use of benzodiazepines as selective blockers of the $I_{Ks}$. Further $I_{Ks}$ blockers are described in FEBS Letters 396 (1996), 271–275: "Specific blockade of slowly activating $I_{sK}$ channels by chromanols . . . " and Pfl ügers, Arch.—Eur. J. Physiol. 429 (1995), 517–530: "A new class of inhibitors of cAMP-mediated Cl⁻ secretion in rabbit colon, acting by the reduction of cAMP-activated K⁺ conductance." The water solubility of the compounds described there, however, is less than that of the compounds of the present invention.

The compounds of the formula I according to the invention and their physiologically tolerable salts can thus be used in animals, preferably in mammals, and in particular in humans, as pharmaceuticals per se, in mixtures with one another, or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments with K⁺ channel-blocking action. Furthermore, the present invention relates to pharmaceutical compositions which as active constituent contain an effective dose of at least one compound of the formula I and/or of a physiologically tolerable salt thereof in addition to customary, pharmaceutically acceptable carriers, innocuous excipients and auxiliaries. The pharmaceutical preparations normally contain 0.1 to 90 percent by weight of the compounds of the formula I and/or of their physiologically tolerable salts. The pharmaceutical preparations can be prepared in a manner known per se. For this purpose, the compounds of the formula I and/or their physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain compounds of the formula I according to the invention and/or their physiologically tolerable salts can be administered orally, parenterally, e.g. intravenously, rectally, by inhalation or topically, the preferred administration being dependent on the individual case, e.g. the particular course of the illness to be treated.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, agents for achieving a depot effect, buffer substances or colorants.

The compounds of the formula I can also be combined with other pharmaceutical active compounds to achieve an advantageous therapeutic effect. Thus in the treatment of cardiovascular disorders advantageous combinations with substances having cardiovascular activity are possible. Possible combination components of this type which are advantageous for cardiovascular disorders are, for example, other antiarrhythmics, i.e. class I, class II or class III antiarrhythmics, such as, for example $I_{Kr}$ channel blockers, e.g. dofetilide, or furthermore hypotensive substances such as ACE inhibitors (for example enalapril, captopril, ramipril), angiotensin antagonists, K⁺ channel activators and also alpha- and beta-receptor blockers, but also sympathomimetic compounds and compounds having adrenergic activity, and also Na⁺/H⁺ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with $H_2$ antagonists (e.g. ranitidine, cimetidine, famotidine, etc.), in particular when used for the treatment of gastrointestinal disorders.

For an oral administration form, the active compounds are mixed with the additives suitable for this purpose, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case the preparation can be carried out either as dry or as moist granules. Suitable oily excipients or solvents are, for example, vegetable or animal oils, such as sunflower oil or cod-liver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds, if desired with the substances customary for this such as solubilizers, emulsifiers or further auxiliaries, are brought into solution, suspension or emulsion. The compounds of the formula I and their physiologically tolerable salts can also be lyophilized and the lyophilizates obtained can be used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also additionally contain other pharmaceutical auxiliaries such as surfactants, emulsifiers and stabilizers as well as a propellant. Such a preparation contains the active compound customarily in a concentration from approximately 0.1 to 10, in particular from approximately 0.3 to 3 percent by weight.

The dose of the active compound of the formula I or of the physiologically tolerable salts thereof to be administered depends on the individual case and, as customary, is to be adapted for an optimum effect to the conditions of the individual case. Thus it depends, of course, on the frequency of administration and on the potency and duration of action of the compounds employed in each case for therapy or prophylaxis, but also on the nature and severity of the disease to be treated and on the sex, age, weight and individual responsiveness of the human or animal to be treated and on whether the therapy is acute or prophylactic. Customarily, the daily dose of a compound of the formula I in the case of administration to a patient approximately 75 kg in weight is at least 0.001 mg/kg of body weight, preferably at least 0.01 mg/kg of body weight, in particular at least 0.1 mg/kg of body weight, up to at most 100 mg/kg of body weight, preferably up to at most 20 mg/kg of body weight, in particular up to at most 1 mg/kg of body weight. In other words, the preferred dose range is from about 0.001 to about 100 mg/kg, more preferrably from about 0.01 to about 20 mg/kg, most preferrably from about 0.1 to about 1 mg/kg. The dose can be administered in the form of an individual dose or divided into several, e.g. two, three or four, individual doses. In particular in the treatment of acute cases of cardiac arrhythmias, for example in an intensive care unit, parenteral administration by injection or infusion, e.g. by an intravenous continuous infusion, can also be advantageous.

The compounds of the formula I and their physiologically tolerable salts selectively inhibit K$^+$ (cAMP) channels and I$_{Ks}$ channels. On account of this property, apart from use as pharmaceutical active compounds in human medicine and veterinary medicine, they can also be employed as a scientific tool or as aids for biochemical investigations in which an effect on potassium channels is intended, and also for diagnostic purposes, e.g. in the in vitro diagnosis of cell or tissue samples. They can further be employed, as already mentioned above, as intermediates for the preparation of other pharmaceutical active compounds.

Explanation of the abbreviations used in the text

| DMA | dimethylacetamide |
| HMPT | hexamethylphosphoramide |
| TMU | tetramethylurea |
| h | hour(s) |
| M | mol |
| MCPBA | m-chloroperbenzoic acid |
| mM | millimol |

-continued

| min | minutes |
| TEA | triethylamine |
| THF | tetrahydrofuran |
| NBS | N-bromosuccinimide |
| NCS | N-chlorosuccinimide |

EXAMPLE 1

Ethanesulfonic acid (3-hydroxy-2,2-dimethyl-3,4-dihydro-2H-pyrano[3,2-c]pyridin-4-yl)methylamide

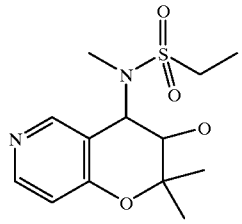

A solution of 480 mg (3.5 mmol) of N-methylethylsulfonamide in 0.75 ml DMSO (dimethylsulfoxide) is added to a suspension of 27 mg (0.7 mmol) of NaH (60% strength) in 1.5 ml of DMSO. After stirring at room temperature for 2 h, a solution of 0.48 g (2.7 mmol) of 2,2-dimethyl-1a,7b-dihydro-2H-1,3-dioxa-6-aza-cyclo-propa[a]naphthalene (prepared analogously to G. Burell et al. J. Med. Chem. 33 (1990) 3023–3027) in 6 ml of DMSO is added dropwise. The mixture is heated at 60° C. for 4 h and then stirred overnight at room temperature. The reaction mixture is added to ice water and extracted with ethyl acetate. After removing the solvent in vacuo, the solid obtained is stirred with a mixture of heptane and ethyl acetate and filtered off with suction. 400 mg (67%) of ethanesulfonic acid (3-hydroxy-2,2-dimethyl-3,4-dihydro-2H-pyrano[3,2-c]pyridin-4-yl)methylamide are obtained as a solid (m.p. 163° C.).

We claim:
1. A compound of formula I:

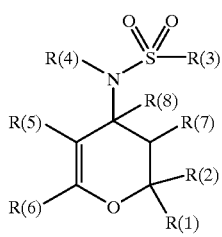

in which:
R(1) and R(2) independently of one another are hydrogen, CF$_3$, C$_2$F$_5$, C$_3$F$_7$, alkyl having 1, 2, 3, 4, 5, or 6 carbon atoms, or phenyl,
  wherein said phenyl is unsubstituted or substituted by 1 or 2 identical or different substituents that are F, Cl, Br, I, CF$_3$, methyl, methoxy, sulfamoyl, or methylsulfonyl;
or
R(1) and R(2) together are an alkylene chain having 2, 3, 4, 5, 6, 7, 8, 9, or 10 carbon atoms;
  where one CH$_2$ group of the alkylene chain can be replaced by —O—, —CO—, —S—, —SO—, —SO$_2$—, or —NR(10)—;

17

R(10) is hydrogen or alkyl having 1, 2, or 3 carbon atoms;
R(3) is R(12)—$C_aH_{2a}$[NR(13)]$_m$—;
R(12) is hydrogen or cycloalkyl having 3, 4, 5, 6, 7, or 8 carbon atoms, $CF_3$, $C_2F_5$, or $C_3F_7$;
a is zero, 1, 2, 3, 4, 5, 6, 7, 8, 9, or 10;
m is zero or 1;
R(13) is hydrogen or alkyl having 1, 2, 3, 4, 5, or 6 carbon atoms;

or

R(12) and R(13) together are an alkylene chain having 4, 5, 6, 7, or 8 carbon atoms,
where one $CH_2$ group of the alkylene chain can be replaced by —O—, —[SO$_{zero, 1\ or\ 2}$]—, —CO—, or —NR(10)—;
R(10) is hydrogen or alkyl having 1, 2, or 3 carbon atoms;
R(4) is R(14)—$C_rH_{2r}$;
r is zero, 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;
where one $CH_2$ group of the group $C_rH_{2r}$ can be replaced by —O—, —CH=CH—, —C≡C—, —CO—, —CO—O—, —CO—NR(11)—, —[SO$_{zero, 1, or\ 2}$]—, or —NR(11)—;
R(11) is hydrogen or —($C_aH_{2a}$)—R(10);
where one $CH_2$ group of the group $C_aH_{2a}$ can be replaced by —O—, —CH=CH—, —C≡C—, —CO—, —CO—O—, —O—CO—, —S—, —SO—, —SO$_2$—, —NR(10)—, or —CONR(10)—;
R(10) is hydrogen or alkyl having 1, 2, or 3 carbon atoms;
a is zero, 1, 2, 3, 4, 5, 6, 7, 8, 9, or 10;

or

R(3) and R(4) together are an alkylene chain having 3, 4, 5, 6, 7, or 8 carbon atoms, where one $CH_2$ group of the alkylene chain can be replaced by —O—, —[SO$_{zero, 1, or\ 2}$]—, —CO—, or —NR(11)—;
R(11) is hydrogen or —($C_aH_{2a}$)—R(10),
where one $CH_2$ group of the group $C_aH_{2a}$ can be replaced by —O—, —CH=CH—, —C≡C—, —CO—, —CO—O—, —O—CO—, —S—, —SO—, —SO$_2$—, NR(10)—, or —CONR(10)—;
R(10) is hydrogen or alkyl having 1, 2, or 3 carbon atoms;
a is zero, 1, 2, 3, 4, 5, 6, 7, 8, 9, or 10;
R(5) and R(6) together are
—CR(15)=CR(16)—CR(17)=N—,
—CR(15)=CR(16)—N=CR(17)—,
—CR(15)=N—CR(17)=N—,
—CR(15)=N—N=CR(17)—,
—N=CR(16)—CR(17)=N—, or
—S—CR(15)=CR(16)—;
R(15), R(16) and R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21),
R(22)—$C_sH_{2s}$—Z—, or phenyl,

18 wherein said phenyl is unsubstituted or substituted by 1 or 2 identical or different substituents that are F, Cl, Br, I, $CF_3$, methyl, methoxy, sulfamoyl, or methylsulfonyl;
R(19) is hydrogen or alkyl having 1, 2, or 3 carbon atoms;
R(21) is hydrogen, methyl, ethyl, phenyl, or —$C_uH_{2u}$—NR(19)R(20);
wherein said phenyl is unsubstituted or substituted by 1 or 2 identical or different substituents that are F, Cl, Br, I, $CF_3$, methyl, methoxy, sulfamoyl, or methylsulfonyl;
R(20) is hydrogen or alkyl having 1, 2, or 3 carbon atoms;
u is 2 or 3;
R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
wherein said phenyl is unsubstituted or substituted by 1 or 2 identical or different substituents that are F, Cl, Br, I, $CF_3$, methyl, methoxy, sulfamoyl, or methylsulfonyl;
s is zero, 1, 2, 3, 4, 5, or 6;
Z is —[S(O)$_{zero, 1, or\ 2}$]—, —CO—, —SO$_{(zero, 1, or\ 2)}$—NR(11)—, —SO$_2$—O—, —O—, —NR(11)— or —[CO—NR(11)]—;
R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms;
R(8) is hydrogen or alkyl having 1, 2, 3, 4, 5, or 6 carbon atoms;

or a physiologically tolerable salt of a compound of formula I.

2. A compound of the formula I as claimed in claim 1, in which:
R(1) and R(2) independently of one another are hydrogen, $CF_3$, $C_2F_5$, $C_3F_7$, alkyl having 1, 2, 3, 4, 5, or 6 carbon atoms, or phenyl,
wherein said phenyl is unsubstituted or substituted by 1 or 2 identical or different substituents that are F, Cl, Br, I, $CF_3$, methyl, methoxy, sulfamoyl, or methylsulfonyl;

or

R(1) and R(2) together are an alkylene chain having 2, 3, 4, 5, 6, 7, 8, 9, or 10 carbon atoms;
where one $CH_2$ group of the alkylene chain can be replaced by —O—, —CO—, —S—, —SO—, —SO$_2$—, or —NR(10)—;
R(10) is hydrogen or alkyl having 1, 2, or 3 carbon atoms;
R(3) is R(12)—$C_aH_{2a}$[NR(13)]$_m$—;
R(12) is hydrogen or cycloalkyl having 3, 4, 5, 6, 7, or 8 carbon atoms, $CF_3$, $C_2F_5$, or $C_3F_7$;
a is zero, 1, 2, 3, 4, 5, 6, 7, 8, 9, or 10;
m is zero or 1;
R(13) is hydrogen or alkyl having 1, 2, 3, 4, 5, or 6 carbon atoms;
R(4) is R(14)—$C_rH_{2r}$;
r is zero, 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl, wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;

where one $CH_2$ group of the group $C_rH_{2r}$ can be replaced by —O—, —CH=CH—, —C≡C—, —CO—, —CO—O—, —CO—NR(11)—, —[SO$_{zero, 1\ or\ 2}$]—, or —NR(11)—;

R(11) is hydrogen or —($C_aH_{2a}$)—R(10)
where one $CH_2$ group of the group $C_aH_2a$ can be replaced by —O—, —CH=CH—, —C≡C—, —CO—, —CO—O—, —O—CO—, —S—, —SO—, —SO$_2$—, NR(10)—, or —CONR(10)—;

a is zero, 1, 2, 3, 4, 5, 6, 7, 8, 9, or 10;

R(5) and R(6) are
—CR(15)=CR(16)—CR(17)=N—,
—CR(15)=CR(16)—N=CR(17)—,
—CR(15)=N—CR(17)=N—,
—CR(15)=N—N=CR(17)—,
—N=CR(16)—CR(17)=N—, or
—S—CR(15)=CR(16)—;

R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
wherein said phenyl is unsubstituted or substituted by 1 or 2 identical or different substituents that are F, Cl, Br, I, $CF_3$, methyl, methoxy, sulfamoyl, or methylsulfonyl;

R(19) is hydrogen or alkyl having 1, 2, or 3 carbon atoms;

R(21) is hydrogen, methyl, ethyl, phenyl, or —$C_uH_{2u}$—NR(19)R(20);
wherein said phenyl is unsubstituted or substituted by 1 or 2 identical or different substituents that are F, Cl, Br, I, $CF_3$, methyl, methoxy, sulfamoyl, or methylsulfonyl;

u is 2 or 3;

R(20) is hydrogen or alkyl having 1, 2, or 3 carbon atoms;

R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
wherein said phenyl is unsubstituted or substituted by 1 or 2 identical or different substituents that are F, Cl, Br, I, $CF_3$, methyl, methoxy, sulfamoyl, or methylsulfonyl;

s is zero, 1, 2, 3, 4, 5, or 6;

Z is —[S(O)$_{zero, 1, or 2}$]—, —CO—, —SO$_2$—NR(11)—, —SO$_2$—O—, —O—, —NR(11)—, or —[CO—NR(11)]—;

R(7) is hydrogen, hydroxyl, alkoxy having 1, 2, 3, or 4 carbon atoms, acyloxy having 1, 2, 3 or 4 carbon atoms, Cl, Br, F, or alkyl having 1, 2, 3, or 4 carbon atoms;

R(8) is hydrogen or alkyl having 1, 2, 3, 4, 5, or 6 carbon atoms;

or a physiologically tolerable salt of a compound of formula I.

3. A compound of the formula I as claimed in claim 1, in which:

R(1) and R(2) independently of one another are hydrogen, $CF_3$, $C_2F_5$, $C_3F_7$, alkyl having 1, 2, 3, 4, 5, or 6 carbon atoms, or phenyl,
wherein said phenyl is unsubstituted or substituted by 1 or 2 identical or different substituents that are F, Cl, Br, I, $CF_3$, methyl, methoxy, sulfamoyl, or methylsulfonyl;

or

R(1) and R(2) together are an alkylene chain having 2, 3, 4, 5, 6, 7, 8, 9, or 10 carbon atoms;
where one $CH_2$ group of the alkylene chain can be replaced by —O—, —CO—, —S—, —SO—, —SO$_2$—, or —NR(10)—;

R(10) is hydrogen or alkyl having 1, 2, or 3 carbon atoms;

R(3) is R(12)—$C_aH_{2a}$[NR(13)]$_m$—;

R(12) is hydrogen or cycloalkyl having 3, 4, 5, 6, 7, or 8 carbon atoms, $CF_3$, $C_2F_5$, or $C_3F_7$;

a is zero, 1, 2, 3, 4, 5, 6, 7, 8, 9, or 10;

m is zero or 1;

R(13) is hydrogen or alkyl having 1, 2, 3, 4, 5, or 6 carbon atoms;

R(4) is R(14)—$C_rH_{2r}$;

r is 1, 2, 3, 4, 5, 6, 7, 8, 9, 10, 11, 12, 13, 14, 15, 16, 17, 18, 19, or 20;

R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;

where one $CH_2$ group of the group $C_rH_{2r}$ can be replaced by —O—, —CH=CH—, —C≡C—, —CO—, —CO—O—, —CO—NR(11)—, —[SO$_{zero, 1, or 2}$]—, or —NR(11)—;

R(11) is hydrogen or —($C_aH_{2a}$)—R(10);
where one $CH_2$ group of the group $C_aH_{2a}$ can be replaced by —O—, —CH=CH—, —C≡C—, —CO—, —CO—O—, —O—CO—, —S—, —SO—, —SO$_2$—, —NR(10)—, or —CONR(10)—;

R(10) is hydrogen or alkyl having 1, 2, or 3 carbon atoms;

a is zero, 1, 2, 3, 4, 5, 6, 7, 8, 9, or 10;

R(5) and R(6) are
—CR(15)=CR(16)—CR(17)=N— or
—CR(15)=CR(16)—N=CR(17)—;

R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
wherein said phenyl is unsubstituted or substituted by 1 or 2 identical or different substituents that are F, Cl, Br, I, $CF_3$, methyl, methoxy, sulfamoyl, or methylsulfonyl;

R(19) is hydrogen or alkyl having 1, 2, or 3 carbon atoms;

R(21) is hydrogen, methyl, ethyl, phenyl, or —$C_uH_{2u}$—NR(19)R(20);
wherein said phenyl is unsubstituted or substituted by 1 or 2 identical or different substituents that are F, Cl, Br, I, $CF_3$, methyl, methoxy, sulfamoyl, or methylsulfonyl;

R(20) is hydrogen or alkyl having 1, 2, or 3 carbon atoms;

u is 2 or 3;

R(22) is hydrogen, cycloalkyl having 3, 4, 5, 6, 7, or 8 carbon atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, or $C_3F_7$, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
s is zero, 1, 2, 3, 4, 5, or 6;
Z is —[S(O)$_{zero, 1, or 2}$]—, —CO—, —$SO_2$—NR(11)—, —$SO_2$—O—, —O—, —NR(11)—, or —[CO—NR(11)]—;
R(7) is hydrogen, hydroxyl, alkoxy having 1, 2, 3, or 4 carbon atoms, alkyl having 1, 2, 3, or 4 carbon atoms;
R(8) is hydrogen or alkyl having 1, 2, 3, 4, 5, or 6 carbon atoms;
or a physiologically tolerable salt of a compound of formula I.

4. A compound of the formula I as claimed in claim 1 in which:
  R(1) and R(2) independently of one another are hydrogen, $CF_3$, $C_2F_5$, $C_3F_7$, alkyl having 1, 2, 3, 4, 5, or 6 carbon atoms, or phenyl,
    wherein said phenyl is unsubstituted or substituted by 1 or 2 identical or different substituents that are F, Cl, Br, I, $CF_3$, methyl, methoxy, sulfamoyl, or methylsulfonyl;
  or
  R(1) and R(2) together are an alkylene chain having 2, 3, 4, 5, or 6 carbon atoms;
    where one $CH_2$ group of the alkylene chain can be replaced by —O—, —CO—, —S—, —SO—, —$SO_2$—, or —NR(10)—;
  R(10) is hydrogen or alkyl having 1, 2, or 3 carbon atoms;
  R(3) is R(12)—$C_aH_{2a}$—;
  R(12) is hydrogen or cycloalkyl having 3, 4, 5, 6, 7, or 8 carbon atoms, $CF_3$, $C_2F_5$, or $C_3F_7$;
  a is zero, 1, 2, 3, 4, 5, 6, 7, 8, 9, or 10;
  R(4) is R(14)—$C_rH_{2r}$—;
  r is 1, 2, 3, 4, 5, 6, 7, 8, 9, 10, 11, 12, or 13;
  R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
    wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;
  where one $CH_2$ group of the group $C_rH_{2r}$ can be replaced by —O—, —CH=CH—, —C≡C—, —CO—, —CO—O—, —CO—NR(11)—, —[SO$_{zero, 1, or 2}$]—, or —NR(11)—;
  R(11) is hydrogen or —($C_aH_{2a}$)—R(10)
    where one $CH_2$ group of the group $C_aH_{2a}$ can be replaced by —O—, —CH=CH—, —C≡C—, —CO—, —CO—O—, —O—CO—, —S—, —SO—, —$SO_2$—, NR(10)—, or —CONR(10)—;
  R(10) is hydrogen or alkyl having 1, 2, or 3 carbon atoms;
  R(5) and R(6) are
    —CR(15)=CR(16)—CR(17)=N— or
    —CR(15)=CR(16)—N=CR(17)—;
  R(15), R(16), R(17) independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
R(19) is hydrogen or alkyl having 1, 2, or 3 carbon atoms;
R(21) is hydrogen, methyl, ethyl, or phenyl,
  wherein said phenyl is unsubstituted or substituted by 1 or 2 identical or different substituents that are F, Cl, Br, I, $CF_3$, methyl, methoxy, sulfamoyl, or methylsulfonyl;
R(22) is hydrogen;
s is zero, 1, 2, 3, 4, 5, or 6;
Z is —[S(O)$_{zero, 1, or 2}$]—, —CO—, —$SO_2$—NR(11)—, —$SO_2$—O—, —O—, —NR(11)—, or —[CO—NR(11)]—;
R(7) is hydrogen, hydroxyl, alkoxy having 1, 2, 3, or 4 carbon atoms, alkyl having 1, 2, 3, or 4 carbon atoms;
R(8) is hydrogen or alkyl having 1, 2, 3, 4, 5, or 6 carbon atoms;
or a physiologically tolerable salt of a compound of formula I.

5. A process for preparing a compound of formula I as claimed in claim 1, which comprises the step of reacting a compound of formula II

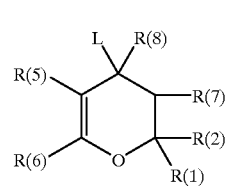

II in which R(1), R(2), R(5), R(6), R(7) and R(8) have the meaning indicated in formula I and L is a nucleofugic leaving group,
with a sulfonamide of the formula IIII or a salt thereof:

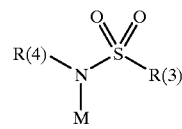

III in which R(3) and R(4) have the meaning indicated in formula I and M is hydrogen or a metal atom, to yield a compound of formula I.

6. A process of claim 5, in which the nucleofugic leaving group L of formula II is F, Cl, Br, I, $MeSO_2$—O—, or a p-toluenesulfonyloxy radical.

7. A process of claim 5, in which R(7) and L of formula II together are an epoxide ring.

8. A process of claim 5, in which M of formula III is lithium, sodium, or potassium.

9. A process for preparing a compound of formula I as claimed in claim 1, which comprises the step of reacting a compound of formula IV

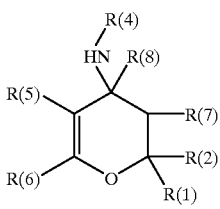

in which R(1), R(2), R(4), R(5), R(6), R(7), and R(8) have the meaning indicated in formula I,
with a sulfonic acid derivative of formula V

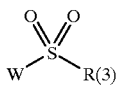

in which R(3) has the meaning indicated in formula I and W is a nucleofugic leaving group.

10. A process of claim 9, in which W is fluorine, bromine, 1-imidazolyl, or chlorine.

11. A process for preparing a compound of formula I as claimed in claim 1, which comprises the step of alkylating a compound of formula VI

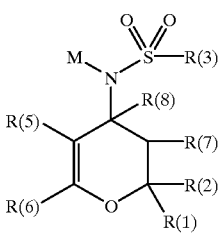

in which R(1), R(2), R(3), R(5), R(6), R(7), and R(8) have the meaning indicated in formula I and M is hydrogen or a metal atom, with an alkylating agent of formula VII

R(4)—L        VII in which L is a nucleofugic leaving group, and
R(4) is R(14)—$C_rH_{2r}$;
r is 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
wherein said phenyl is unsubstituted or substituted by 1 or 2 identical or different substituents that are F, Cl, Br, I, $CF_3$, methyl, methoxy, sulfamoyl, methylsulfonyl, or methylsulfonylamino;
where one $CH_2$ group of the group $C_rH_{2r}$ can be replaced by —O—, —CH=CH—, —C≡C—, —CO—, —CO—O—, —CO—NR(11)—, —[$SO_{zero, 1, or 2}$]— or —NR(11)—;
R(11) is hydrogen or —($C_aH_{2a}$)—R(10);
where one $CH_2$ group of the group $C_aH_{2a}$ can be replaced by —O—, —CH=CH—, —C≡C—, —CO—, —CO—O—, —O—CO—, —S—, —SO—, —$SO_2$—, —NR(10)—, or —CONR(10)—;
R(10) is hydrogen or alkyl having 1, 2, or 3 carbon atoms;
a is zero, 1, 2, 3, 4, 5, 6, 7, 8, 9, or 10;
or R(4) is R(14), wherein
R(14) is cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
wherein said phenyl is unsubstituted or substituted by 1 or 2 identical or different substituents that are F, Cl, Br, I, $CF_3$, methyl, methoxy, sulfamoyl, or methylsulfonyl, or methylsulfonylamino;
to yield a compound of formula I.

12. A process of claim 11 in which M of formula VI is lithium, sodium, or potassium.

13. A process of claim 11 in which L of formula VII is F, Cl, Br, $MeSO_2$—O—, or a p-toluenesulfonyloxy radical.

14. A process for derivitizing a compound of formula I as claimed in claim 1, in which at least one of R(15), R(16), and R(17) of the compound of formula I is hydrogen, comprising the step of effecting an electrophilic substitution reaction at a carbon atom bound to said hydrogen.

15. A pharmaceutical composition which comprises at least one compound as claimed in claim 1, together with at least one pharmaceutical carrier.

16. A method of treating or preventing a $K^+$ channel mediated disease comprising administering to a host in need of such treatment or prevention an effective amount of at least one compound as claimed in claim 1.

17. A method of treating or preventing a cardiac arrhythmia, comprising administering to a host in need of such treatment or prevention an effective amount of at least one compound as claimed in claim 1.

18. A method of claim 17, wherein the cardiac arrhythmia is an atrial, ventricular, or supraventricular arrhythmia, or a reentry arrhythmia.

19. A method of claim 17, wherein the cardiac arrhythmia can be eliminated by action potential prolongation.

20. A method of treating or preventing an atrial fibrillation or an atrial flutter, comprising administering to a host in need of such treatment or prevention an effective amount of at least one compound as claimed in claim 1.

21. A method of inhibiting gastric acid secretion in a human or animal patient comprising administering to the patient in need of such inhibition an effective amount of at least one compound as claimed in claim 1.

22. A method of treating a gastric ulcer or an ulcer of an intestinal region of a human or animal patient comprising administering to the patient in need of such treatment an effective amount of at least one compound as claimed in claim 1.

23. A method of treating or preventing reflux esophagitis, comprising administering to a host in need of such treatment or prevention an effective amount of at least one compound as claimed in claim 1.

24. A method of treating or preventing a diarrheal illness, comprising administering to a host in need of such treatment or prevention an effective amount of at least one compound as claimed in claim 1.

25. A method of preventing sudden heart death resulting from ventricular fibrillation in a human or animal patient comprising administering to the patient in need of such prevention an effective amount of at least one compound as claimed in claim 1.

26. A method of treating cardiac insufficiency in a human or animal patient comprising administering to the patient in need of such treatment an effective amount of at least one compound as claimed in claim 1.

27. A method of claim 26, in which the cardiac insufficiency is a result of congestive heart failure.

28. A method of blocking a calcium channel, which is opened by cyclic adenosine monophosphate, in a human or animal patient comprising administering to the patient in need of such blocking an effective amount of at least one compound as claimed in claim 1.

* * * * *

UNITED STATES PATENT AND TRADEMARK OFFICE
CERTIFICATE OF CORRECTION

PATENT NO. : 6,184,221 B1
DATED : February 6, 2001
INVENTOR(S) : Uwe Gerlach et al.

It is certified that error appears in the above-identified patent and that said Letters Patent is hereby corrected as shown below:

Column 19, claim 2,
Line 10, "$C_aH_2a$" should read -- $C_aH_{2a}$ --.

Column 22, claim 5,
Line 43, "formula III1" should read -- formula III --.

Signed and Sealed this

Second Day of April, 2002

Attest:

Attesting Officer

JAMES E. ROGAN
Director of the United States Patent and Trademark Office